United States Patent [19]

Hoffman et al.

[11] Patent Number: 5,019,053
[45] Date of Patent: May 28, 1991

[54] HYPODERMIC SYRINGE

[75] Inventors: J. Kenneth Hoffman, Warren, Pa.; Joseph W. Blake, III, New Canaan, Conn.

[73] Assignee: GTE Products Corporation, Stamford, Conn.

[21] Appl. No.: 425,138

[22] Filed: Oct. 23, 1989

[51] Int. Cl.⁵ ............................................. A61M 5/315
[52] U.S. Cl. ..................................... 604/220; 604/241
[58] Field of Search ............... 604/232, 233, 187, 240, 604/241, 220

[56] References Cited

U.S. PATENT DOCUMENTS

| | | | |
|---|---|---|---|
| 1,987,146 | 1/1935 | Hein | 604/233 |
| 3,128,765 | 4/1964 | Tint | 604/232 |
| 4,367,738 | 1/1983 | Legendre et al. | 604/218 |
| 4,758,232 | 7/1988 | Chak | 604/220 |

Primary Examiner—John D. Yasko
Attorney, Agent, or Firm—William H. McNeill

[57] ABSTRACT

A disposable hypodermic syringe including a cartridge having a threaded end to which is fastened a hub coupled to a needle. The opposite end of the cartridge is configured to receive a finger grasp. A piston rod has one end which extends through the finger grasp and is fastened to a plunger internal of the cartridge. The opposite end of the piston rod includes a head.

1 Claim, 2 Drawing Sheets

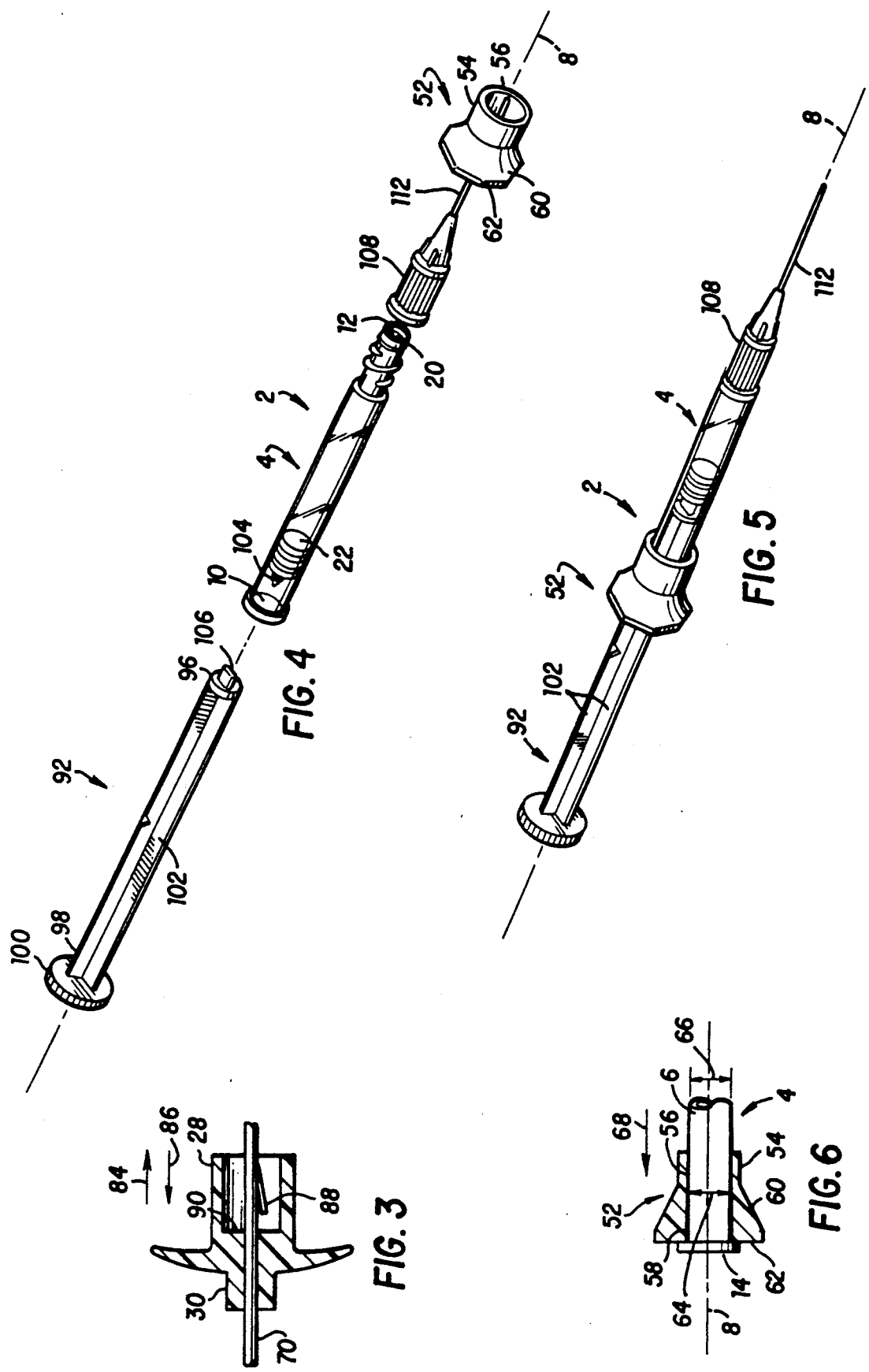

HYPODERMIC SYRINGE

BACKGROUND OF THE INVENTION

1. Field of the Invention

The present invention relates to a dispensable hypodermic syringe for dispensing medicament from or drawing blood into a cartridge having a needle attached to one end thereof and a finger grasp including an actuating device attached to the other end thereof.

2. Description of the Prior Art

One form of hypodermic syringe typically includes a generally cylindrical barrel including a piston rod therein. The rod includes a handle at one end to facilitate reciprocating movement of the rod within the cylindrical barrel. In such a hypodermic syringe a cartridge is provided having a needle attached thereto, the cartridge being inserted into the cylindrical barrel to work in combination with the piston rod to dispense or receive liquid such as medicament or blood, respectively, in response to movement of the piston rod within the barrel. In this form of syringe the piston rod is connected to a plunger in the inserted cartridge, axial movement of the piston rod causing corresponding axial movement of the plunger to dispense the medicament from the cartridge or receive blood within the cartridge depending upon whether such movement is a dispensing or aspirating movement. Such hypodermic needles are well known in the art and examples include embodiments described in U.S. Pat. Nos. 2,524,367 to Smith and 4,744,790 to Jankowski et al.

One problem that occurs during use of such a hypodermic syringe is that of accidental exposure of the user of the syringe to whatever contaminants might be present upon or within the needle or cartridge after use thereof. For example, in those instances where the needle and cartridge are to be removed from the barrel and disposed of, it has been necessary for the user to grasp the needle to the needle and cartridge assembly from the barrel. Such grasping can expose the attendant to any contaminant which is on the exterior surface of the needle and cartridge, particularly if the attendant is not wearing a glove. In addition, not infrequentlY the attendant might be accidentally punctured by the needle while attempting to remove the needle and cartridge and corresponding contamination of the user will obviously result. Somewhat related to these problems is the not unlikely possibility that the attendant might drop the needle and cartridge assembly while removing the assembly from the barrel structure resulting in undesirable contamination of the area exposed to the needle and cartridge. A similar problem is the possibility that the needle and cartridge assembly might prematurely fall out of the barrel like holder during the disposal operation. In any event, accidental contamination of a medical attendant or anyone else can present a serious health problem especially if the contaminant is an infectious disease such as hepatitis, AIDS and the like.

In order to prevent undesirable contamination, it is highly desirable to provide a disposable hypodermic syringe. Similarly, it is also desirable to provide a disposable hypodermic syringe which can be readily assembled for use. A further object is to provide a disposable hypodermic syringe wherein all of the component parts can readily assembled and held rigidly together. Another object is to provide such a disposable hypodermic syringe which can be quickly assembled.

SUMMARY OF THE INVENTION

This invention achieves these and other results by providing a hypodermic syringe comprising a cartridge including an elongated tubular body extending along a longitudinal axis from a first open end to a second open end. The first open end includes an external flange and the second open end includes external threads and an internal septum. The cartridge further includes a piston therein slideable along the longitudinal axis. A finger grasp extends along the longitudinal axis from one open end which communicates with an opposite open end, and the first open end of the cartridge extends into the one open end of the finger grasp. Means is provided associated with the finger grasp and the external flange for holding the cartridge in place relative to the finger grasp. A plunger is provided comprising an elongated rod having one portion for extension through the opposite open end of the finger grasp for coupling to the piston, and an opposite portion which includes a bead. A hub extends along the longitudinal axis and includes internal hub threads for fastening the hub to the cartridge by means of the external cartridge threads. A needle is attached to the hub and extends through the hub along the longitudinal axis. The needle includes a proximal end extending from the hub in one direction of the longitudinal axis for penetrating the internal septum when the internal hub threads are threaded upon the external cartridge threads, and an opposite distal end extending from the hub in an opposite direction of the longitudinal axis.

BRIEF DESCRIPTION OF THE DRAWINGS

FIG. 3 is a view of one end of the embodiment of FIGS. 1 and 2;

FIG. 4 is an exploded view of another embodiment of the present invention:

FIG. 5 is an assembled perspective view of the embodiment of FIG. 4; and

FIG. 6 is a partial view of one end of the embodiment of FIGS. 4 and 5.

DESCRIPTION OF THE PREFERRED EMBODIMENT

Figure 1:
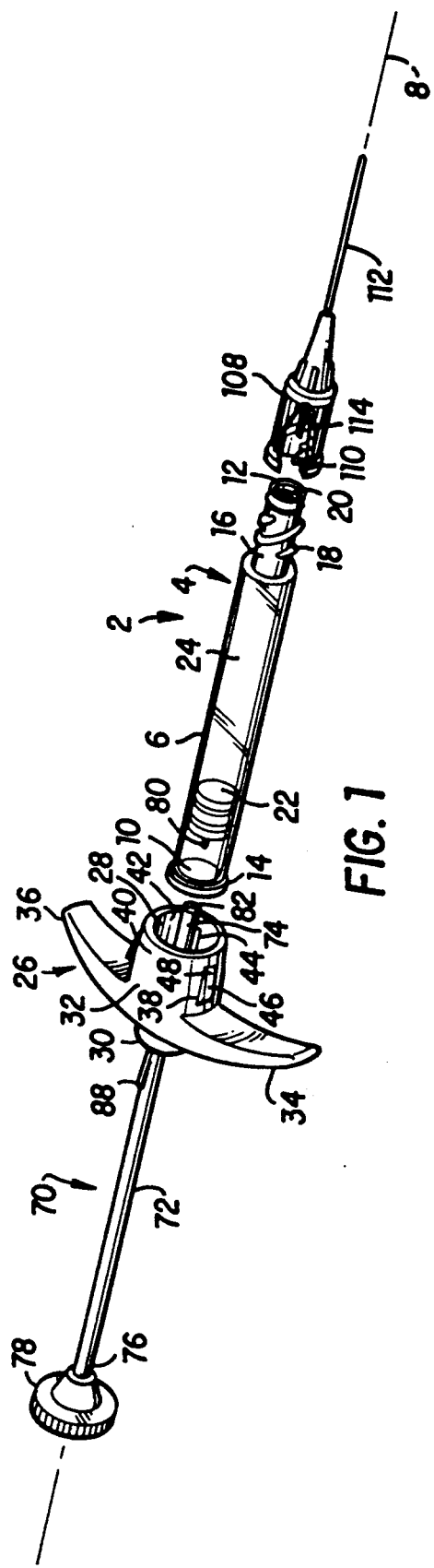
FIG. 1 is an exploded view of one of the present invention.
Figure 2:
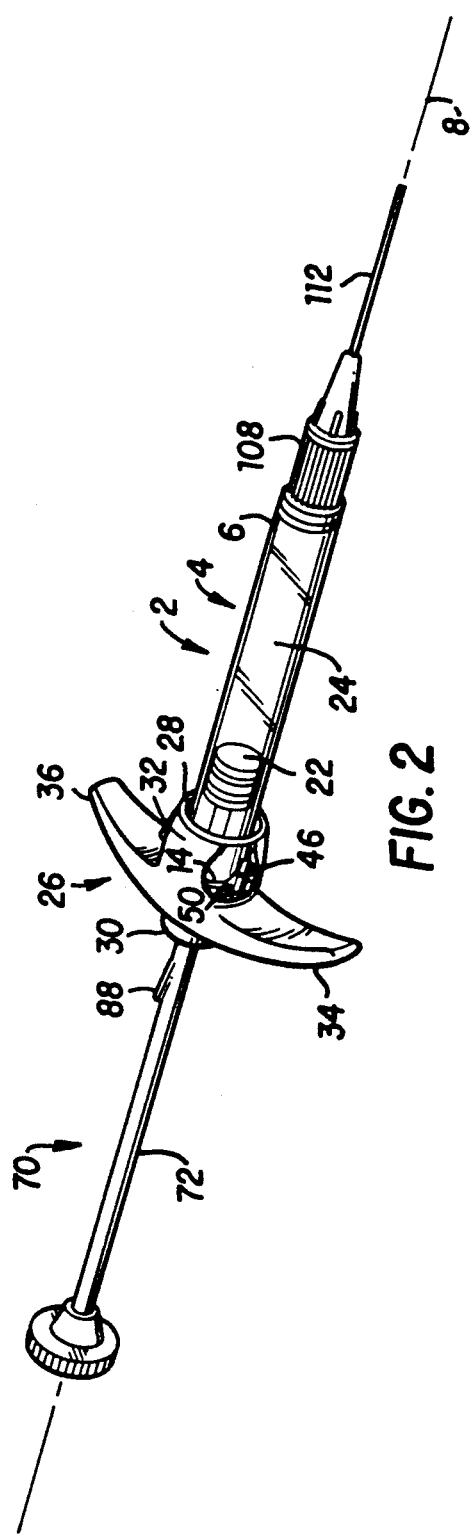
FIG. 2 is an assembled perspective view of the embodiment of FIG. 1.

The embodiments of this invention which are illustrated in FIGS. 1 to 3 are particularly suited for achieving the objects of this invention. FIGS. 1 to 3 depict a hypodermic syringe 2 comprising a cartridge 4 which includes an elongated tubular body 6 extending along a longitudinal axis 8 from a first open end 10 to a second open end 12. The cartridge can be formed from glass or some other known material suitable for use as described herein. The open end 10 includes an external flange 14 extending radially outward relative to axis 8 from the outer perpheral surface of the cartridge 4. The open end 12 includes a neck portion 16 having external threads 18. The open end 12 also includes an internal septum 20 at or near the end of neck portion 16. The septum 20 is a wall or membrane formed from a material such as rubber which can be punctured by a needle as described herein to provide access into the elongated tubular body 6 of the cartridge 4. Cartridge 4 also includes a piston 22 preferably formed from a resilient material. The piston 22 fits tightly within the elongated tubular body 6 to provide a sealed chamber 24 therein between the piston 22 and septum 20 and is also slideable along axis 8 as described herein.

A finger grasp 26 preferably of polypropylene is provided extending along the longitudinal axis 8 from one open end 28 which communicates with an opposite open end 30. In other words, the finger grasp includes an internal opening therethrough from open end 28 to open end 30. The end 10 of cartridge 4 extends into the open end 28 of the finger grasp as depicted in FIG. 2 which is a view of the hypodermic syringe 2 when assembled. Means is associated with the finger grasp 26 and the external flange 14 for holding the cartridge 4 in place relative to the finger grasp when the hypodermic syringe 2 is so assembled. For example, in the embodiment of FIGS. 1 to 3 such a holding means includes at least one locking member which extends into the open end 28 of the finger grasp and engages the external flange 14 of the cartridge. In particular, the finger grasp 26 includes a central hub 32 which extends in the direction of the longitudinal axis 8 from open end 28 to the opposite open end 30. Opposing wings 34 and 36 extend from the central hub 32 in a generally radial direction relative to axis 8. The locking members extend through the central hub 32 into the open end 28. For example, the central hub 32 includes at least one aperture 38 therethrough; that is, aperture 38 extends from the outer peripheral surface 40 of the central hub 32 to the inner surface 42. Each locking member extends through a corresponding aperture 38 and into the cavity 44 formed within the central hub 32 between ends 28 and 30. For example, in the preferred embodiment locking members 46 extend through corresponding apertures 38 into cavity 44. Preferably, the central hub 32 and locking members 46 are formed by a unitary structure and each locking member extends into cavity 44 and is resiliently biased towards the axis 8. This structure can be effected by forming the finger grasp 26 as a unitary structure, the looking members 46 being tabs integrally hinged to the central hub 32 at 48. With such a finger grasp, it is possible to insert the elongated tubular body 6 of the cartridge 4 into open end 28 of the central hub 32 until the outer flange 14 engages an end 50 of the locking members 46. By pushing the body 6 further into the cavity 14, there will be a camming action between the flange 14 and ends 50 by means of which the flange will snap into locking engagement with the ends 50 as depicted in FIG. 2.

Another embodiment is depicted in FIGS. 4 to 6 wherein like numbers designate like parts. In particular, a hypodermic syringe 2 is provided including a cartridge 4 similar to the cartridge 4 of FIGS. 1 to 3. In the embodiment of FIGS. 4 to 6, a finger grasp 52 is also preferably of polypropylene and includes (1) a central hub portion 54 which extends in the direction of longitudinal axis 8 to define an open end 56 of the finger grasp and (2) a flanged portion extending from the central hub portion and including an opposite open end 58 of the finger grasp. Preferably, the flanged portion includes a generally conical section 60 extending from the central hub portion 54 and a cone base portion 62, the opposite open end 58 extending through the cone base portion and the conical section along axis 8 to meet the open end 56 and thereby form a bore which extends through the finger grasp from one end to the opposite end thereof as depicted in FIG. 6. The diameter 64 of the bore, including the ends 58 and 60, is only slightly greater than the diameter 66 of the elongated tubular body 6 of the cartridge 4 to form a tight sliding fit between the elongated tubular body 6 vis-a-vis the bore and open ends 56 and 58. In assembling the embodiment of FIGS. 4 to 6, the finger grasp 52 is slid vis-a-vis the elongated tubular body 6 in the direction of arrow 68 identified in FIG. 6 until the cone base portion 62 abuts the flange 14 of the cartridge 4, the tight fit between body 6 and the finger grasp 52 holding the parts together.

The embodiments of FIGS. 1 to 6 include a plunger comprising an elongated rod having one portion for extension through an open end of finger grasp for coupling to the piston 22, and an opposite portion which includes a head. For example, in the embodiment of FIGS. 1 to 3, a plunger 70 preferably of polypropylene is provided including an elongated rod 72 having one portion 74 which extends through open end 30 and an opposite portion 76 which includes a head 78. In this embodiment, the piston 22 includes a protuberance 80 extending therefrom along axis 8 towards the end 10 of cartridge 4. The portion 74 of rod 72 includes a recess 82 into which the protuberance extends for coupling the piston to the rod. In the embodiment of FIGS. 1 and 2 the protuberance includes external and the recess includes corresponding internal threads to effect such coupling.

The elongated rod 70 includes a locking means extending therefrom for permitting the portion 74 to be extended through open end 30 of the finger grasp in one direction identified by arrow 84 and then preventing portion 74 from being removed from the open end 30 in an opposite direction 86. For example, such locking means includes a resilient tab 88 extending from an outer peripheral surface of the elongated rod 72 at a position located between the portion 74 and head 78. The tab 88 will become depressed to allow the rod to be moved through open end 30 in the direction of arrow 84. Once through the opening, the tab will spring back to its original position so that if the rod 72 is moved in the direction of arrow 86 the tab 88 will abut against the surface 90 to prevent further removal of rod 72.

In the embodiment of FIGS. 4 to 6, a plunger 92 preferably of polypropylene is provided having a portion 96 which extends through open end 58 of the finger grasp 52, and an opposite portion 98 which includes a head 100. In this embodiment, the plunger is formed by a plurality of elongated ribs 102 which extend from head 100 to the portion 96 which extends through open end 58. The piston 22 includes a protuberance 104 and the end 96 includes a recess 106, the protuberance and recess being configured to provide a snap-fit therebetween to effect the coupling of the piston to the plunger.

In the embodiment of FIGS. 1 to 6, a hub 108 is provided which extends along the longitudinal axis 8. Hub 108 includes internal hub threads 110 for fastening the hub to cartridge 4 by means of the corresponding external threads 18 which are associated with the neck portion 16 of the cartridge. A needle 112 is attached to the hub 108 in a known manner. The needle 112 extends along longitudinal axis 8 and includes a proximal end 114 extending from the hub in one direction of the axis for penetrating the internal septum 20 when the internal hub threads 110 are threaded upon the external cartridge threads 18. Needle 12 also includes an opposite distal end 116 which extends from the hub in an opposite direction of axis 8 in the usual manner. Hub 108 can be formed from any suitable material but preferably is metal such as stainless steel. In the preferred embodiment the threads 18 and 110 are fast threads and advance the hub 108 one quarter of an inch for each 360' turn of the hub.

Typically, the embodiments discussed herein will be packaged such that the parts have teen sterilized and placed in a sterilized sealed envelope in a unassembled construction to the extent desired. Whether the assembly of the hypodermic needle 2 occurs partially or wholly before packaging or after removal from the envelope, assembly is accomplished in the following manner. In the embodiment of FIGS. 1 to 3, the finger grasp 26 is snapped upon the cartridge 4 by inserting the flange 14 into the open end 28 until the flange snaps into a locking position vis-a vis the locking 46. The needle 112 is then fastened to the cartridge by threading the hub 108 and its internal threads 110 upon the cartridge external threads 18. As the hub 102 is threaded upon the neck portion 16 of the cartridge, the end 114 of the needle will puncture the septum 20 so that the needle will be in communication with the sealed chamber 24. Finally, the plunger 70 is inserted into the open end 30 of the finger grasp and attached to piston 22 by means of the threaded protuberance 80 and corresponding threaded recess 82. The hypodermic needle is then used to dispense or aspirate in the usual manner. Once the elongated rod 72 has been inserted such that the resilient tab 88 extends beyond the surface 90, it will no longer be possible to remove the rod from the finger grasp 26.

In the embodiment of FIGS. 4 to 6, the finger grasp 52 will be placed over the end 12 of the cartridge 4 such that the end 12 will be inserted through the finger grasp at open end 58. The finger grasp will then be slid along the cartridge until the surface 62 is caused to bear against the flange 14 as depicted in FIG. 6. The assembly of the needle and hub will be the same as discussed above regarding FIGS. 1 to 3. The plunger 92 will be inserted into the open end 58 of the finger grasp 52 and attached to piston 22 by means of a snap-fit between the protuberance 104 of the piston 22 and the recess 106 of the plunger.

The preferred materials for forming the embodiments of the present invention have been discussed herein. However, apparatus of the present invention can be formed from any material useful in the manufacture of hypodermic syringes.

It will be apparent that the present invention provides a disposable hypodermic needle which can be readily assembled for use. The syringe can be assembled quickly and is designed such that the components will be rigidly held together.

The embodiments which have been described herein are but some of several which utilize this invention and are set forth here by way of illustration but not of limitation. It is apparent that many other embodiments which will be readily apparent to those skilled in the art may be made without departing materially from the spirit and scope of this invention.

We claim:
1. A hypodermic syringe, comprising;
 a cartridge including an elongated tubular body extending along a longitudinal axis from a first open ind to a second open end, said first open end including an external flange and said second open end including external threads and an internal septum, said cartridge further including a piston therein slidable along said longitudinal axis;
 a finger grasp extending along said longitudinal axis from one open end which communicates with an opposite open end, said first open end of said cartridge extending into said one open end of said finger grasp;
 holding means associated with said finger grasp and said external flange for holding said cartridge in place relative to said finger grasp, said holding means further including at least one locking member which extends into said one open end of said finger grasp and engages said external flange of said cartridge;
 a plunger comprising an elongated rod having one portion for extension through said opposite open end of said finger grasp for coupling to said piston, and an opposite portion which includes a head;
 a hub extending along said longitudinal axis and including internal threads for fastening said hub to said cartridge by means of external cartridge threads; and
 a needle attached to said hub and extending through said hub along said longitudinal axis and having a proximal end extending from said hub in one direction of said longitudinal axis for penetrating said internal septum when said internal hub threads are threaded upon said external cartridge threads, and an opposite distal end extending from said hub in an opposite direction of said longitudinal axis;
 said finger grasp including (1) a central hub which extends in the direction of said longitudinal axis from said one open end to said opposite open end, and (2) opposing wings extending from said central hub in a generally radial direction relative to said longitudinal axis, said at least one locking member extending through said central hub into said one open end;
 said central hub including at least one aperture extending therethrough, and wherein each locking member of said at least one locking member extends through a corresponding aperture of said at least one aperture into a cavity of said central hub;
 said central hub and each locking member being formed by a unitary structure, and wherein each locking member extends into said cavity and is resiliently biased toward said longitudinal axis.

* * * * *